United States Patent
Peng et al.

(10) Patent No.: US 11,731,925 B2
(45) Date of Patent: Aug. 22, 2023

(54) PROCESS FOR PRODUCING HALOGENATED OLEFINS

(71) Applicant: THE CHEMOURS COMPANY FC, LLC, Wilmington, DE (US)

(72) Inventors: Sheng Peng, Hockessin, DE (US); Mario Joseph Nappa, Leesburg, FL (US); Andrew Jackson, Newark, DE (US); Robert D. Lousenberg, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 1155 days.

(21) Appl. No.: 16/320,320

(22) PCT Filed: Jul. 24, 2017

(86) PCT No.: PCT/US2017/043497
§ 371 (c)(1),
(2) Date: Jan. 24, 2019

(87) PCT Pub. No.: WO2018/022500
PCT Pub. Date: Feb. 1, 2018

(65) Prior Publication Data
US 2019/0233353 A1   Aug. 1, 2019

Related U.S. Application Data

(60) Provisional application No. 62/367,412, filed on Jul. 27, 2016.

(51) Int. Cl.
| | |
|---|---|
| C07C 17/278 | (2006.01) |
| C07C 17/25 | (2006.01) |
| C07C 17/20 | (2006.01) |
| C07C 21/18 | (2006.01) |
| C07C 19/08 | (2006.01) |
| C07C 17/275 | (2006.01) |

(52) U.S. Cl.
CPC .......... *C07C 17/278* (2013.01); *C07C 17/206* (2013.01); *C07C 17/25* (2013.01); *C07C 17/275* (2013.01); *C07C 21/18* (2013.01)

(58) Field of Classification Search
None
See application file for complete search history.

(56) References Cited

U.S. PATENT DOCUMENTS

| | | | |
|---|---|---|---|
| 3,528,500 A | 9/1970 | Brown | |
| 4,560,759 A | 12/1985 | Hiratani | |
| 4,828,818 A | 5/1989 | Carlson et al. | |
| 5,036,036 A | 7/1991 | Lerou | |
| 6,187,978 B1* | 2/2001 | Rygas | C07C 17/278 570/257 |
| 6,291,730 B1* | 9/2001 | Baker | C07C 17/278 570/257 |
| 7,241,928 B2 | 7/2007 | Rao et al. | |
| 2012/0065434 A1* | 3/2012 | Nose | C07C 17/206 570/160 |
| 2014/0058141 A1* | 2/2014 | Nappa | C07C 17/278 570/172 |
| 2014/0114096 A1* | 4/2014 | Nappa | C07C 17/206 570/156 |
| 2016/0046547 A1* | 2/2016 | Jackson | C07C 19/12 570/155 |
| 2016/0107955 A1* | 4/2016 | Filas | C07C 17/272 570/247 |

FOREIGN PATENT DOCUMENTS

| | | | |
|---|---|---|---|
| EP | 486333 | 10/1991 | |
| JP | S52 12102 A | 1/1977 | |
| JP | S5212102 A * | 1/1977 | ........... C07C 17/278 |
| WO | 2008/030442 A1 | 3/2008 | |
| WO | 2010/123148 A1 | 10/2010 | |
| WO | 2012/067865 A1 | 5/2012 | |

OTHER PUBLICATIONS

Machine translation of patent No. JPS5212102A, Jan. 29, 1977, pp. 1-4 (Year: 1977).*
International Search Report and Written Opinion Issued in PCT/US2017/043497 dated Oct. 6, 2017, 15 Ppages.
Barlow et al., Heterocyclic Polyfluoro-Compounds, Part 31. Photochemical Oxetan Formation From Fluoroketones and Perfluoroaldehydes and 1,2-Dofluoroethylene, Published Jan. 1, 1980 in J.C.S Perkins I, pp. 2258-2267.

* cited by examiner

*Primary Examiner* — Medhanit W Bahta

(57) ABSTRACT

Disclosed herein is a process comprising contacting a haloalkane reactant with an olefin in the presence of a catalyst system that consists of metallic iron and a phosphine to produce a haloalkane insertion product, wherein said haloalkane reactant is an alkane substituted with at least one halogen selected from the group consisting of F, Cl, and combinations thereof. Also disclosed herein is a process comprising contacting $CF_3CCl_3$ with $CH_2=CHX$ in the presence of a catalyst system that consists of metallic iron and a phosphine to make $CF_3CCl_2CH_2CHClX$, wherein X=F or Cl. Also disclosed are further reactions in a sequence to produce HFO-1336ze and HCFO-1335zd. Also disclosed herein is a new composition comprising the compound $CF_3CF_2CH=CHCl$.

8 Claims, No Drawings

PROCESS FOR PRODUCING HALOGENATED OLEFINS

BACKGROUND INFORMATION

Field of the Disclosure

This disclosure relates in general to methods of synthesis of fluorinated olefins.

Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, foam blowing agents and propellants. These new compounds, such as HFC refrigerants, HFC-134a and HFC-125, and blowing agents HFC-134a and 245fa being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins and hydrochlorofluoroolefins are believed to meet both goals. Thus there is a need for manufacturing processes that provide halogenated hydrocarbons and fluoroolefins that have a low global warming potential.

SUMMARY

Disclosed herein is a process comprising contacting a haloalkane reactant with an olefin in the presence of a catalyst system that consists of metallic iron and a phosphine to produce a haloalkane insertion product, wherein said haloalkane reactant is an alkane substituted with at least one halogen selected from the group consisting of F, Cl, and combinations thereof.

Also disclosed herein is a process comprising contacting $CF_3CCl_3$ with $CH_2=CHX$ in the presence of a catalyst system that consists of metallic iron and a phosphine to make $CF_3CCl_2CH_2CHClX$, wherein X=F or Cl. Also disclosed are further reactions in a sequence to produce HFO-1336ze and/or HCFO-1335zd.

Also disclosed herein is a new composition comprising the compound $CF_3CF_2CH=CHCl$.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Aspects of the present disclosure are directed to a metal catalyzed olefin insertion process that includes the use of a metal and a ligand to obtain a desired product, such as a haloalkane insertion product, by insertion of an olefin into a haloalkane reactant. In particular, some aspects are directed to an iron and triphenyl phosphine catalytic system for olefin insertion of haloalkanes with a high rate of conversion and selectivity.

In one embodiment, an olefin insertion process is provided comprising contacting a haloalkane reactant with an olefin in the presence of a catalyst system that consists of metallic iron and a phosphine to produce a haloalkane insertion product, wherein said haloalkane reactant is an alkane substituted with at least one halogen selected from the group consisting of F, Cl, and combinations thereof.

In some embodiments, the haloalkane reactant is selected from the group consisting of chlorocarbons, hydrochlorocarbons, chlorofluorocarbons, hydrochlorofluorocarbons, and hydrofluorocarbons.

In one embodiment, chlorocarbons are compounds having only carbon and chlorine, including but not limited to carbon tetrachloride ($CCl_4$), perchloroethane ($CCl_3CCl_3$), and the like.

In one embodiment, hydrochlorocarbons are compounds having carbon, hydrogen, and chlorine, including but not limited to chloromethane ($CH_3Cl$), methylene chloride ($CH_2Cl_2$), trichloromethane ($CHCl_3$), chloroethane ($CH_3CH_2C_1$), dichloroethane ($CH_3CHCl_2$ or $CH_2ClCH_2Cl$), and the like.

In one embodiment, chlorofluorocarbons are compounds having carbon, hydrogen, fluorine, and chlorine, including but not limited to dichlorodifluoromethane ($CCl_2F_2$), trichlorofluoroethane ($CCl_3F$), 1,1,1-trichloror-2,2,2-trifluoroethane (CFC-113a, $CF_3CCl_3$), 1,1,2-trichloror-1,2,2-trifluoroethane (CFC-113, $CF_2ClCFCl_2$), and the like.

In one embodiment, hydrochlorofluorocarbons are compounds having carbon, hydrogen, fluorine, and chlorine, including but not limited to chlorodifluoromethane ($CHF_2Cl$), dichlorofluoromethane ($CHFCl_2$), chlorofluoromethane ($CH_2FCl$), 2,2-dichloro-1,1,1-trifluoroethane ($CHCl_2CF_3$), 1,2-dichloro-1,1,2-trifluoroethane ($CHFClClF_2$), 2,2-dichloro-1,1,2-trifluoroethane ($CHF_2CFCl_2$), 2-chloro-1,1,1,2-tetrafluoroethane ($CHFClCF_3$), and the like.

In one embodiment, hydrochlorofluorocarbons are compounds having carbon, hydrogen, and fluorine, including but not limited to trifluoromethane ($CHF_3$), difluoromethane ($CH_2F_2$), fluoromethane ($CH_3F$), 1,1-difluoroethane ($CHF_2CH_3$), 3,3,3-trifluoroethane ($CF_3CH_3$), 1,1,1,2-tetrafluoroethane ($CH_2FCF_3$), 1,1,2,2,-tetrafluoroethane ($CHF_2CHF_2$), pentafluoroethane ($CF_3CHF_2$), and the like.

In one embodiment, the haloalkane reactant is a C1 to C5 compound. In another embodiment, the haloalkane reactant is a C1, C2 or C3 compound.

In one embodiment, the olefin is an unsaturated hydrocarbon, with at least one double bond, optionally substituted with Cl, F or combinations thereof. In another embodiment, the olefin is selected from the group consisting of vinyl chloride ($CH_2=CHCl$), ethylene ($CH_2=CH_2$), 3,3,3-trifluoropropene ($CF_3CH=CH_2$), vinyl fluoride ($CH_2=CHF$), vinylidene chloride ($CH_2=CCl_2$), vinylidene fluoride ($CH_2=CF_2$), allyl chloride ($CH_2=CHCH_2Cl$), and the like.

In one embodiment, each component of the iron and phosphine catalytic systems has a particular concentration with respect to the moles of olefinic reactant used. As such, in some embodiments, a ratio of the number of moles of halocarbon reactant to moles of olefin is from about 3:1 to 1:1. In another embodiment, the molar ratio of halocarbon reactant to moles of olefin is from about 2.25:1 to 1:1. In another embodiment, the molar ratio of halocarbon reactant to moles of olefin is from about 2:1 to 1.1.

In one embodiment, a ratio of the number of moles of iron to the number of moles of olefin is from about 0.01:1 to 0.1:1. In another embodiment, the molar ratio of iron to olefin is from about 0.03:1 to 0.06:1. In another embodiment, the ratio of iron to olefin is from about 0.07:1 to 0.1:1. For example, the molar ratio of iron powder to vinyl chloride may be from 0.03-0.06 moles of iron to every one mole of olefin, while in another example, the molar ratio is from 0.07-0.1 moles of iron to every mole of vinyl chloride. In yet another example, a ratio of iron to vinyl chloride may be 0.0465:1, while in a further example, the ratio of iron to vinyl chloride may be 0.093:1.

In one aspect of the disclosure, a number of moles of phosphine ligand may be measured in relation to a number of moles of olefin present in the reaction system. For example, in one embodiment, a molar ratio of phosphine ligand to olefin may be from about 0.01:1 to 0.04:1. In another embodiment, the molar ratio of phosphine ligand to olefin may be from about 0.02:1 to 0.06:1. For example, the molar ratio of phosphine ligand to olefin may be 0.023:1, while in another example, the molar ratio of phosphine ligand to olefin may be 0.046:1. In one aspect of the invention, the molar ratio of triphenyl phosphine to vinyl chloride is 0.023:1, while in another example, the molar ratio of triphenyl phosphine to vinyl chloride is 0.046:1.

In one embodiment, the insertion reaction may be carried out at an elevated temperature. In another embodiment, the insertion reaction may be carried out at a temperature between about 50° C. and 250° C. In another embodiment, the insertion reaction may be carried out at a temperature between about 100° C. and 200° C. In another embodiment, the reaction may be carried out at a temperature between about 120° C. and 180° C. In another embodiment, the reaction may be carried out at a temperature between about 130° C. and 170° C.

In one embodiment, olefin insertion reactions with 1,1,1-trichloror-2,2,2-trifluoroethane (CFC-113a, $CF_3CCl_3$) can be utilized to make compounds of interest to the fluorochemicals industry at this time, $CF_3CF_2CH=CHF$ (1,3,3,4,4,4-hexafluoro-1-butene, HFO-1336ze) and $CF_3CF_2CH=CHCl$ (1-chloro-3,3,4,4,4-pentafluoro-1-butene, HCFO-1335zd). These compounds have low GWP, low toxicity, non-flammability and other desirable characteristics that make them useful in fluorochemical applications. HFO-1336ze (either E or Z isomer) may be used as a foam expansion agent, refrigerant, working fluid for high temperature heat pump and power cycles, such as organic Rankine cycles. HCFO-1335zd (either E or Z isomer) may be useful as a fire extinguishant, solvent, refrigerant, working fluids for high temperature heat pumps and power cycles, such as organic Rankine cycles.

Both of these compounds exist as an E-isomer or a Z-isomer and some of each may be present at a low level in any sample of either isomer. The processes disclosed herein selectively produce E-HFO-1336ze and E-HCFO-1335zd at about 90%.

HFO-1335zd is a new compound. Therefore, disclosed herein, in one embodiment, is a composition comprising the compound $CF_3CF_2CH=CHCl$. In certain embodiments, $CF_3CF_2CH=CHCl$ is the E isomer, Z isomer or a combination thereof.

The present disclosure describes a process for production of HFO-1336ze and HCFO-1335zd by way of a two-step or a three-step process route that provide improved conversion and selectivity over prior disclosed processes.

The two-step process involves an insertion reaction of either vinyl fluoride ($CH_2=CHF$, VF) or vinyl chloride ($CH_2=CHCl$, VC) and CFC-113a, followed by a gas phase fluorination by reaction with HF in the presence of catalyst as shown below.

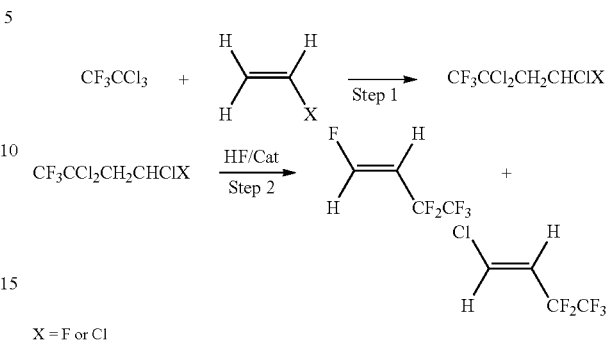

X = F or Cl

Step 1 of the reaction comprises contacting $CF_3CCl_3$ with $CH_2=CHX$ in a reaction zone in the presence of metallic iron catalyst and a phosphine ligand to make $CF_3CCl_2CH_2CHClX$, wherein X=F or Cl. This step may be conducted in a liquid-phase reactor operating in batch, semi-batch, semi-continuous, or continuous modes.

In one embodiment, of the olefin insertion process, the haloalkane reactant is $CF_3CCl_3$, the olefin is $CH_2=CHF$ and the haloalkane insertion product is $CF_3CCl_2CH_2CHClF$.

In another embodiment, of the olefin insertion process, the haloalkane reactant is $CF_3CCl_3$, the olefin is $CH_2=CHCl$ and the haloalkane insertion product is $CF_3CCl_2CH_2CHCl_2$.

In one embodiment, the insertion reaction may be conducted in a reaction zone comprising any reaction vessel of appropriate size for the scale for the reaction. In one embodiment, the reaction zone is a reaction vessel comprised of materials which are resistant to corrosion. In one embodiment, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings. In another embodiment, the reaction vessel may be made of other materials of construction including stainless steels, in particular of the austenitic type, and copper-clad steel.

In certain embodiments, the metallic iron component of the catalyst may be from any source (including a combination of sources) of an iron component and may be iron powder, iron wire, iron screen or iron turnings.

In some embodiments, the phosphine ligand may be an alkylphosphine or arylphosphine, including but not limited to triphenyl phosphine, tributyl phosphine and the like. In one embodiment, the phosphine ligand comprises triphenylphosphine. In another embodiment, the phosphine ligand consists essentially of triphenylphosphine. In another embodiment, the phosphine ligand consists of triphenylphosphine.

In one embodiment, each component of the iron and phosphine catalytic systems has a particular concentration with respect to the moles of olefinic reactant used. As such, in some embodiments, a ratio of the number of moles of CFC-113a to moles of VF or VC is from about 3:1 to 1:1. In another embodiment, the molar ratio of CFC-113 to VF or VC is from about 2.25:1 to 1:1. In another embodiment, the molar ratio of CFC-113 to VF or VC is from about 2:1 to 1:1.

In one embodiment, a ratio of the number of moles of iron to the number of moles of VF or VC is from about 0.01:1 to 0.1:1. In another embodiment, the molar ratio of iron to VF or VC is from about 0.03:1 to 0.06:1. In another embodiment, the ratio of iron to VF or VC is from about 0.07:1 to 0.1:1. For example, the molar ratio of iron powder to vinyl chloride may be from 0.03-0.06 moles of iron to every one mole of olefin, while in another example, the molar ratio is from 0.07-0.1 moles of iron to every mole of vinyl chloride. In yet another example, a ratio of iron to vinyl chloride may be 0.0465:1, while in a further example, the ratio of iron to vinyl chloride may be 0.093:1.

In one aspect of the disclosure, a number of moles of phosphine ligand may be measured in relation to a number of moles of VF or VC present in the reaction system. For example, in one embodiment, a molar ratio of phosphine ligand to VF or VC may be from about 0.01:1 to 0.04:1. In another embodiment, the molar ratio of phospine ligand to VF or VC may be from about 0.02:1 to 0.06:1. For example, the molar ratio of phospine ligand to olefin may be 0.023:1, while in another example, the molar ratio of ligand to olefin may be 0.046:1. In one aspect of the invention, the molar ratio of triphenyl phosphine to vinyl chloride is 0.023:1, while in another example, the molar ratio of triphenyl phosphine to vinyl chloride is 0.046:1.

In one embodiment, the insertion reaction may be carried out at an elevated temperature. In another embodiment, the insertion reaction may be carried out at a temperature between about 50° C. and 250° C. In another embodiment, the insertion reaction may be carried out at a temperature between about 100° C. and 200° C. In another embodiment, the reaction may be carried out at a temperature between about 120° C. and 180° C. In another embodiment, the reaction may be carried out at a temperature between about 130° C. and 170° C.

Byproducts in the olefin insertion reaction would be higher VC or VF inserted telomers, such as $CF_3CCl_2(CH_2CHX)_2Cl$.

In another embodiment of the olefin insertion process, the haloalkane reactant is $CF_3CCl_3$, the olefin is $CH_2=CHCF_3$ and the haloalkane insertion product is $CF_3CCl_2CH_2CHClCF_3$.

In another embodiment of the olefin insertion process, the haloalkane reactant is $CCl_4$, the olefin is $CH_2=CH_2$ and the haloalkane insertion product is $CCl_3CH_2CH_2Cl$.

In another embodiment of the olefin insertion process, the haloalkane reactant is $CF_3CCl_3$, the olefin is $CH_2=CCl_2$ and the haloalkane insertion product is $CF_3CCl_2CH_2CCl_3$.

In another embodiment of the olefin insertion process, the haloalkane reactant is $CF_3CCl_3$, the olefin is $CH_2=CF_2$ and the haloalkane insertion product is $CF_3CCl_2CH_2CClF_2$.

In another embodiment of the olefin insertion process, the haloalkane reactant is $CF_3CCl_3$, the olefin is $CH_2=CHCH_2Cl$ and the haloalkane insertion product is $CF_3CCl_2CH_2CHClCH_2Cl$.

Step 2 of the process comprises contacting $CF_3CCl_2CH_2CHClX$ with HF in the gas phase in the presence of catalyst to make $CF_3CF_2CH=CHF$ and $CF_3CF_2CH=CHCl$. In one embodiment the catalyst is a chrome catalyst.

Useful catalysts for the process include chromium-based catalysts, such as chromium oxyfluoride, which catalyst may either be unsupported, or supported on a support such as activated carbon, graphite, fluoride graphite, or fluoride alumina. The chromium catalyst may either be used alone, or in the presence of a co-catalyst selected from nickel, cobalt, manganese or zinc salt. In one embodiment, a chromium catalyst is high surface area chromium oxide, or chromium/nickel on fluoride alumina ($Cr/Ni/AlF_3$), the preparation of which is reported in European Patent EP 486,333.

The chromium oxyfluoride catalysts can be made by treating $Cr_2O_3$ (chromium oxide) with HF, $CCl_3F$ or hydrofluorocarbons. In one embodiment of this invention, a chromium oxyfluoride catalyst is made by treating dry $Cr_2O_3$ with a fluorination agent such as $CCl_3F$ or HF. This treatment can be accomplished by placing the $Cr_2O_3$ in a suitable container (which can be the reactor to be used to perform the fluorination reaction) and thereafter passing HF over the dry $Cr_2O_3$ for a suitable period of time (e.g., about 15 to 300 minutes) at a suitable temperature (e.g., about 200° C. to 450° C.).

In another embodiment of this invention, a chromium oxyfluoride catalyst is made by treating $Cr_2O_3$ with a hydrofluorocarbon at an elevated temperature. In another embodiment of this invention, a chromium oxyfluoride catalyst is made in situ. For example, the reactant HFC-E-1234ze can be employed in the formation of a chromium oxyfluoride catalyst by heating together with $Cr_2O_3$ in the reactor. $Cr_2O_3$ is commercially available from Engelhard Corporation (101 Wood Avenue, P.O. Box 770, Iselin, N.J. 08830-0770).

$Cr_2O_3$ can also be prepared by pyrolysis of ammonium dichromate as disclosed in U.S. Pat. No. 5,036,036, which is incorporated herein by reference.

$Cr_2O_3$ can also be prepared by the reaction of chromium (VI) oxide with a reducing solvent, such as methanol, as disclosed in U.S. Pat. No. 4,828,818, which is incorporated herein by reference.

$Cr_2O_3$ can also be prepared by reducing chromium (VI) oxide in water with a suitable reducing agent, such as ethanol, as disclosed in U.S. Pat. No. 3,258,500, which is incorporated herein by reference.

The chromium catalysts are preferably activated before use, typically by a procedure whereby the catalyst is heated to from 350 to 400° C. under a flow of nitrogen for a period of time, after which the catalyst is heated under a flow of HF and nitrogen or air for an additional period of time.

In one embodiment, the gas phase fluorination may be conducted in a reaction zone comprising any reaction vessel of appropriate size for the scale for the reaction. In one embodiment, the reaction zone is a reaction vessel comprised of materials which are resistant to corrosion. In one embodiment, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings. In another embodiment, the reaction vessel may be made of other materials of construction including stainless steels, in particular of the austenitic type, and copper-clad steel.

The molar ratio of HF to organic fed to the reaction zone is, in one embodiment, from about 6:1 to about 25:1. In another embodiment, the molar ratio of HF to organic fed to the reaction zone is, in one embodiment, from about 10:1 to about 20:1.

In one embodiment, contact time for the fluorination reaction may be from about 2 seconds to about 80 seconds. In another embodiment, contact time for the fluorination reaction may be from about 10 seconds to about 60 seconds. In another embodiment, contact time for the fluorination reaction may be from about 20 seconds to about 50 seconds.

In one embodiment, suitable temperatures for the reaction zone for the fluorination reaction are from about 120° C. to about 200° C. In another embodiment, suitable temperatures for the reaction zone are from about 150° C. to about 180° C.

In one embodiment, the pressure in the reaction zone for the fluorination reaction may be from about 0 to 200 psig. In another embodiment, the pressure in the reaction zone may be from about 30 to 180 psig.

For the fluorination reaction the reactor effluent will contain excess HF, HCl and the reaction products HFO-1336ze and HCFO-1335zd. It is likely that some of the starting material, $CF_3CCl_2CH_2CHClX$, will also be in the reactor effluent.

The reaction product is a mixture of compounds that may be isolated by via fractionation distillation. Excess acids may be removed via distillation or scrubbing as needed.

The three-step process also involves an insertion reaction of CFC-113a and either vinyl fluoride ($CH_2$=CHF, VF) or vinyl chloride ($CH_2$=CHCl, VC), but is followed by a liquid phase fluorination by reaction with HF in the presence of fluorination catalyst, and a liquid phase dehyrodrohalogenation as shown below.

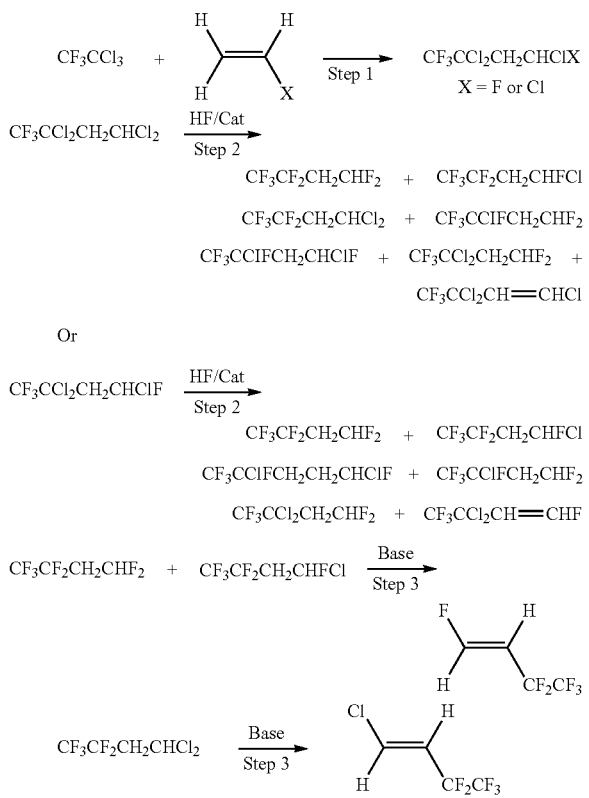

Step 1 for the three-step process is the same CFC-113a insertion into VF or VC as described previously herein.

Step 2 for the three-step process comprises contacting $CF_3CCl_2CH_2CHClX$ (wherein X=F or Cl) with HF in the liquid phase in the presence of a second fluorination catalyst to make a mixture of compounds comprising at least one of $CF_3CF_2CH_2CHF_2$ (also referred to as HFC-347mcf), $CF_3CF_2CH_2CHFCl$ (also referred to as HCFC-346mcf), or $CF_3CF_2CH_2CHCl_2$ (also referred to as HCFC-345mcf). This step may be conducted in a liquid-phase reactor operating in batch, semi-batch, semi-continuous, or continuous modes.

In one embodiment, the liquid phase fluorination may be conducted in a reaction zone comprising any reaction vessel of appropriate size for the scale for the reaction. In one embodiment, the reaction zone is a reaction vessel comprised of materials which are resistant to corrosion. In one embodiment, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings. In another embodiment, the reaction vessel may be made of other materials of construction including stainless steels, in particular of the austenitic type, and copper-clad steel.

The molar ratio of HF to organic fed to the reaction zone is, in one embodiment, from about 6:1 to about 30:1. In another embodiment, the molar ratio of HF to organic fed to the reaction zone is, in one embodiment, from about 10:1 to about 25:1.

The second fluorination catalyst may be any catalyst useful in the liquid phase fluorination step, including Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $NiF_5$, $FeCl_3$ and combinations of two or more of these. It is noted that $SbF_5$ is a liquid at low temperature.

Non-exclusive examples of liquid phase fluorination catalysts are antimony halide, tin halide, tantalum halide, titanium halide, niobium halide, molybdenum halide, iron halide, fluorinated chrome halide, fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, fluorinated species of $SbCl_5$, fluorinated species of $SbCl_3$, fluorinated species of $SnCl_4$, fluorinated species of $TaCl_5$, fluorinated species of $TiCl_4$, fluorinated species of $NbCl_5$, fluorinated species of $MoCl_6$, fluorinated species of $FeCl_3$, or combinations thereof.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

In one embodiment, the liquid phase fluorination catalyst (or second fluorination catalyst) is selected from the group consisting of $SbF_5$, $SnCl_4$, $TaCl_5$, $TiCl_4$, $NbCl_5$, and fluorinated species thereof. In another embodiment, the liquid phase fluorination catalyst (or second fluorination catalyst) is selected from the group consisting of $SbF_5$, $SnCl_4$, $TaCl_5$, $TiCl_4$ and/or fluorinated species thereof. In another embodiment the liquid phase fluorination catalyst (or second fluorination catalyst) is $SbF_5$.

The amount of catalyst relative to HF in the reaction zone is, in one embodiment, maybe from about 0.1 mole percent to 10 mole percent. In another embodiment, the amount of catalyst relative to HF in the reaction zone is, in one embodiment, maybe from about 0.5 mole percent to 5 mole percent, in particular, when the catalyst is $SbF_5$.

In some embodiments, when $SbF_5$ is the catalyst, the liquid phase fluorination may be run at temperatures from about 30° C. to 120° C. In another embodiment, when $SbF_5$ is the catalyst, the liquid phase fluorination may be run at temperatures from about 40° C. to 110° C. In another embodiment, when $SbF_5$ is the catalyst, the liquid phase fluorination may be run at temperatures from about 50° C. to 100° C.

In some embodiments, when a tantalum catalyst is used, the liquid phase fluorination may be run at temperatures from about 75° C. to 200° C. In another embodiment, when a tantalum catalyst is used, the liquid phase fluorination may be run at temperatures from about 85° C. to 180° C. In another embodiment, when a tantalum catalyst is used, the liquid phase fluorination may be run at temperatures from about 100° C. to 160° C.

In some embodiments, when a titanium catalyst is used, the liquid phase fluorination may be run at temperatures from about 40° C. to 120° C. In another embodiment, when a titanium catalyst is used, the liquid phase fluorination may be run at temperatures from about 50° C. to 110° C. In another embodiment, when a titanium catalyst is used, the liquid phase fluorination may be run at temperatures from about 60° C. to 100° C.

In some embodiments, when a niobium catalyst is used, the liquid phase fluorination may be run at temperatures from about 90° C. to 250° C. In another embodiment, when a niobium catalyst is used, the liquid phase fluorination may be run at temperatures from about 100° C. to 220° C. In another embodiment, when a niobium catalyst is used, the liquid phase fluorination may be run at temperatures from about 120° C. to 200° C.

In one embodiment, the liquid phase fluorination reaction when the starting material is $CF_3CCl_2CH_2CHCl_2$ (also referred to as HCFC-343mab) will produce $CF_3CF_2CH_2CHCl_2$ (also referred to as HCFC-345mcf), and may also produce at least one of $CF_3CClFCH_2CHF_2$ (also referred to as HCFC-345mbf), $CF_3CClFCH_2CHClF$ (also referred to as HCFC-344mbf), $CF_3CCl_2CH_2CHF_2$ (also referred to as HFC-345maf), or $CF_3CCl_2CH=CHCl$ (also referred to as HCFO-1333zd).

In another embodiment, the liquid phase fluorination reaction when the starting material is $CF_3CCl_2CH_2CHClF$ (also referred to as HCFC-344maf) will produce at least one of $CF_3CF_2CH_2CHF_2$ or $CF_3CF_2CH_2CHFCl$, and may also produce at least one of $CF_3CClFCH_2CHClF$ (also referred to as HCFC-344mbf), $CF_3CClFCH_2CHF_2$ (also referred to as HCFC-345mbf), $CF_3CCl_2CH_2CHF_2$ (also referred to as HFC-345maf), and $CF_3CCl_2CH=CHF$ (also referred to as HCFO-1334maz). These additional products of the reaction may be recycled back to the liquid phase fluorination reaction zone for further fluorination. Isolation of the desired products may be accomplished through fractional distillation of the reactor effluent. Then the desired products may be fed to the next step in the reaction sequence. Excess acid may be removed at this point or carried into the next step where it will be neutralized by aqueous base.

Step 3 of the three-step process comprises contacting at least one of $CF_3CF_2CH_2CHF_2$, $CF_3CF_2CH_2CHFCl$, or $CF_3CCl_2CH_2CHCl_2$ with aqueous base in the presence of a phase transfer catalyst to make at least one of $CF_3CF_2CH=CHF$ (HFO-1336ze) or $CF_3CF_2CH=CHCl$ (HCFO-1335zd).

When $CF_3CF_2CH_2CHF_2$ is contacted with aqueous base, as in this step 3 reaction, dehydrohalogenation produces $CF_3CF_2CH=CHF$ (HFO-1336ze).

When $CF_3CF_2CH_2CHFCl$ is contacted with aqueous base, as in this step 3 reaction, dehydrohalogenation also produces $CF_3CF_2CH=CHF$ (HFO-1336ze).

When $CF_3CCl_2CH_2CHCl_2$ is contacted with aqueous base, as in this step 3 reaction, dehydrohalogenation produces $CF_3CF_2CH=CHCl$ (HCFO-1335zd).

This step may be conducted in a liquid-phase reactor operating in batch, semi-batch, semi-continuous, or continuous modes.

In one embodiment, the dehydrohalogenation may be conducted in a reaction zone comprising any reaction vessel of appropriate size for the scale for the reaction. In one embodiment, the reaction zone is a reaction vessel comprised of materials which are resistant to corrosion. In one embodiment, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings. In another embodiment, the reaction vessel may be made of other materials of construction including stainless steels, in particular of the austenitic type, and copper-clad steel.

In one embodiment, the base in the aqueous base solution is selected from the group consisting of hydroxide, oxide, carbonate, or phosphate salts of alkali metals, alkaline earth metals, and mixtures thereof. In one embodiment, bases which may be used include without limitation lithium hydroxide, sodium hydroxide, potassium hydroxide, calcium hydroxide, magnesium oxide, calcium oxide, sodium carbonate, potassium carbonate, sodium phosphate, potassium phosphate, or the like and mixtures thereof.

As used herein, the aqueous base solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the aqueous base solution contains small amounts of organic liquids which may be miscible or immiscible with water. In some embodiments, the liquid medium in the aqueous base solution is at least 90% water. In one embodiment the water is tap water; in other embodiments the water is deionized or distilled water.

The amount of base (in the aqueous base solution) required by the liquid phase dehydrohalogenation reaction step is approximately the stoichiometric quantity or about 1 mole of base to one mole of organic. In one embodiment, it may desirable (e.g., to increase reaction rate) to employ a ratio of base to organic of greater than one. In some embodiments, large excesses of base (in the basic aqueous solution) are to be avoided as further reaction of the desired product may occur. Thus, in some embodiments, it may be necessary to employ an amount of base (in the basic aqueous solution) that is slightly below the stoichiometric amount so as to minimize secondary reactions. Thus, in one embodiment, the molar ratio of base (in the aqueous base solution) to organic is from about 0.75:1 to about 10:1. In another embodiment, the molar ratio of base (in the aqueous base solution) to organic is from about 0.9:1 to about 5:1. In another embodiment, the molar ratio of base to organic is from about 1:1 to about 4:1. In another embodiment, the molar ratio of base to organic is from about 1:1 to about 1.2:1.

In one embodiment, a solid base (e.g., KOH, NaOH, LiOH or mixtures thereof) is dissolved in water, or alternatively, a concentrated solution of a base (e.g., 50% by weight aqueous potassium hydroxide) is diluted to the desired concentration with water.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrohalogenation reaction.

In some embodiments, the phase transfer catalyst can be ionic or neutral. In one embodiment, the phase transfer catalyst is selected from the group consisting of crown ethers, onium salts, cryptands and polyalkylene glycols and mixtures and derivatives thereof.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. In some embodiments, it is preferred to match crown ether phase transfer catalysts with certain bases used in the basic aqueous solutions. In one embodiment, crown ethers include 18-crown-6, is used in combination with potassium hydroxide basic aqueous solution; 15-crown-5, is used in combination with sodium hydroxide basic aqueous solution; 12-crown-4, is used in combination with lithium hydroxide basic aqueous solution. Derivatives of the above crown ethers are also useful, e.g., dibenzo-18-crown-6, dicyclohexano-18-crown-6, and dibenzo-24-crown-8 as well as 12-crown-4. Other polyethers particularly useful in combination with basic aqueous solution made from alkali metal compounds, and especially for lithium, are described in U.S. Pat. No. 4,560,759 the disclosure of which is herein incorporated by reference. Other compounds analogous to the crown ethers and useful for the same purpose are compounds which differ by the replacement of one or more of the oxygen atoms by other kinds of donor atoms, particularly N or S, such as hexamethyl-[14]-4,11-dieneN$_4$.

In some embodiments, onium salts include quaternary phosphonium salts and quaternary ammonium salts that may be used as the phase transfer catalyst in the process of the present invention; such compounds can be represented by the following formulas II and III:

  (II)

  (III)

wherein each of $R^1$, $R^2$, $R^3$ and $R^4$, which may be the same or different, is an alkyl group, an aryl group or an aralkyl group, and X' is selected from the group consisting of F, Cl, Br, I, OH, $CO_3$, $HCO_3$, $SO_4$, $HSO_4$, $H_2PO_4$, $HPO_4$ and $PO_4$. Specific examples of these compounds include tetramethylammonium chloride, tetramethylammonium bromide, benzyltriethylammonium chloride, methyltrioctylammonium chloride, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In one embodiment, benzyltriethylammonium chloride is used under strongly basic conditions. Other useful compounds within this class of compounds include those exhibiting high temperature stabilities (e.g., up to about 200° C.) including 4-dialkylaminopyridinium salts, tetraphenylarsonium chloride, bis[tris(dimethylamino)phosphine]iminium chloride, and tetratris[tris(dimethylamino)phosphinimino]phosphonium chloride; the latter two compounds are also reported to be stable in the presence of hot, concentrated sodium hydroxide and, therefore, can be particularly useful.

In some embodiments, polyalkylene glycol ethers are useful as phase transfer catalysts. In some embodiments, the polyalkylene glycol ethers can be represented by the formula:

  (IV)

wherein $R^5$ is an alkylene group containing two or more carbons, each of $R^6$ and $R^7$, which may be the same or different, is a hydrogen atom, an alkyl group, an aryl group or, an aralkyl group, and t is an integer of at least 2. Such compounds include, for example glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether. Among them, compounds wherein both R—$^6$ and R—$^7$ are alkyl groups, aryl groups or aralkyl groups are preferred.

In other embodiments, cryptands are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—OCH$_2$CH$_2$—) groups as in 2.2.2-cryptand (4,7,13,16,21,24-hexaoxa-1,10-diazabicyclo-(8.8.8)hexacosane; available under the brand names Cryptand™ 222 and Kryptofix™ 222). The donor atoms of the bridges may all be O, N, or S, or the compounds may be mixed donor macrocycles in which the bridge strands contain combinations of such donor atoms.

Combinations and mixtures of the above described phase transfer catalysts from within one of the groups may also be useful as well as combinations or mixtures two or more phase transfer catalysts selected from more than one group, for example, crown ethers and oniums, or from more than two of the groups, e.g., quaternary phosphonium salts and quaternary ammonium salts, and crown ethers and polyalkylene glycol ethers.

In one embodiment, the amount of phase transfer catalyst used will be from about 0.001 to about 10 mole percent based on the total amount of base present. In another embodiment, the amount of phase transfer catalyst used will be from about 0.01 to about 5 mole percent based on the total amount of base present. In yet another embodiment, the amount of phase transfer catalyst used will be from about 0.05 to about 5 mole percent based on the total amount of base present.

In one embodiment, the liquid phase dehydrohalogenation reaction is conducted at a temperature of from about 0° C. to 120° C. In another embodiment, the liquid phase dehydrohalogenation reaction is conducted at a temperature of from about 20° C. to 100° C. In another embodiment, the liquid phase dehydrohalogenation reaction is conducted at a temperature of from about 30° C. to 80° C.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Iron powder, vinyl chloride, Aliquat® 336 (a quarternary ammonium salt), potassium hydroxide, and sodium hydroxide are all available from Sigma Aldrich (St. Louis, Mo., USA). CFC-113a ($CF_3CCl_3$), vinyl fluoride, hydrogen fluoride, $SbCl_5$, $TaCl_5$ and 3,3,3-trifluoropropene are purchased from Synquest Labs, Inc. (Alachua, Fla., USA).

Legend
CFC-113a=$CF_3CCl_3$ or 1,1,1-trichloro-2,2,2-trifluoroethane
HFO-1336ze=$CF_3CF_2CH$=CHF or 1,3,3,4,4,4-hexafluoro-1-butene
HCFO-1335zd=$CF_3CF_2CH$=CHCl or 1-chloro-3,3,4,4,4-pentafluoro-1-butene

Example 1

Insertion of CFC-113a to Make $CF_3CCl_2CH_2CHCl_2$

Vinyl chloride, $CH_2$=CHCl (22.6 g, 0.354 mol) was added to a mixture of CFC-113a (100 g, 0.53 mol), Fe powder (0.62 g, 0.011 mol) and triphenyl phosphine (1.41 g, 0.0054 mol) in a 210 mL Hastelloy® reactor. The reactor was heated up to 150° C. for 5 hours. The mixture was transferred to a container and analyzed by GC: conversion of CFC-113a was 100% and selectivity to product, $CF_3CCl_2CH_2CHCl_2$ was 90%. (b.p. 71~92° C./63 torr; $^1H$ NMR (CDCl3, 400 MHz) δ 6.14 (t, J=5.5 Hz, 1H), 3.24 (d, J=5.5 Hz, 2H); $^{19}F$ NMR (CDCl3, 376 MHz) δ −80.08 (s, 3F); MS (EI): 212 ($M^+$-Cl))

Example b 2

Insertion of CFC-113a to Make $CF_3CCl_2CH_2CHClF$

Vinyl fluoride (16.3 g, 0.354 mol) was added to a mixture of CFC-113a (100 g, 0.53 mol), Fe powder (0.62 g, 0.011 mol) and triphenyl phosphine (1.41 g, 0.0054 mol) in a 210 mL Hastelloy® reactor. The reactor was heated up to 150° C. for 3 hours. The mixture was transferred to a container and analyzed by GC: conversion of CFC-113a was 100% and selectivity to product, $CF_3CCl_2CH_2CHClF$, was 87.4%. ($^1H$ NMR (500 MHz, CDCl$_3$): δ 6.61 (ddd, 1H, CHFCl, $^2J_{H-F}$=50.7 Hz, $^3J_{H-H}$=7.4, 2.3 Hz), 3.26-3.17 (m, 1H, CH$_2$), 3.06-2.96 (m, 1H, CH$_2$); $^{19}F$ NMR (470 MHz, CDCl$_3$): δ −80.04 (d, 3F, CF$_3$, $^5J_{F-F}$=2.5 Hz), −129.16 to −129.49 (m, 1F, CHFCl); $^{13}C$ NMR (126 MHz, CDCl$_3$): δ 121.7 (q, CF$_3$, $^1J_{C-F}$=282 Hz), 97.1 (d, CHFCl, $^1J_{C-F}$=246 Hz), 80.4 (q, CCl$_2$, $^2J_{C-F}$=36.5 Hz), 49.8 (d, CH$_2$, $^2J_{C-F}$=22.5 Hz); MS (EI): 196 ($M^+$-HCl), 198 ($M^+$-HCl), 200 ($M^+$-HCl))

Example 3

Gas Phase Fluorination to Make HFO-1336ze and HCFO-1335zd

An Inconel® pipe (0.5 inch OD, 10 inch length, 0.034 in wall thickness) is filled with 6 cc chrome catalyst. The reactor is heated to the target temperature between 250 to 325° C. $CF_3CCl_2CH_2CHCl_2$ is fed via an ISCO pump (4.27 mL/hr) and a vaporizer controlled at 170° C. HF is fed as gas to the reactor through a master flow controller from a cylinder. HF reacts with organic over the catalyst in the reactor. HF/organics mole ratio is 10:1 and contact time is 10 seconds. The reaction is run at 0 psig. The reactor effluent is analyzed online using an Agilent® 6890 GC/5973 MS to show 95% conversion of the starting material, 70% selectivity to HFO-1336ze and 30% selectivity to HCFO-1335zd.

Example 4

Liquid Phase Fluorination of $CF_3CCl_2CH_2CHCl_2$

A 240 mL Hastelloy® C shaker tube was charged with $SbF_5$ (8 g, 0.037 mol) and cooled to 20° C. with dry ice/acetone. HF (48 g, 2.4 mol) was added and the shaker tube was cooled and evacuated 3 times. $CF_3CCl_2CH_2CHCl_2$ (30 g, 0.12 mol) was added and the shaker tube was purged with $N_2$ three times. The shaker tube was then heated to the desired temperature (see table 1 for different temperatures) and shaken for 20 hours. Once reaction was complete, the shaker tube was cooled to room temperature and 100 mL of ice cold water was injected into shaker tube. Then the shaker tube was heated to 60° C. and all gas phase was vapor transferred to a cylinder and the remaining liquid was poured into a plastic jar. The liquid product was analyzed by GC and the results shown in Table 1.

TABLE 1

Fluorination of $CF_3CCl_2CH_2CHCl_2$ summary of GC area percent data

| | Entry | | |
|---|---|---|---|
| | 1 | 2 | 3 |
| T (° C.) | 50 | 75 | 100 |
| $CF_3CF_2CH_2CF_2H$ | 0% | 60.90% | 42.27% |

TABLE 1-continued

Fluorination of $CF_3CCl_2CH_2CHCl_2$ summary of GC area percent data

| | Entry | | |
|---|---|---|---|
| | 1 | 2 | 3 |
| $CF_3CClFCH_2CF_2H$ | 0% | 4.42% | 6.38% |
| $CF_3CF_2CH_2CClFH$ | 0% | 2.655 | 0% |
| $CF_3CClFCH_2CClFH$ | 0% | 1.90% | 0% |
| $CF_3CF_2CH_2CCl_2H$ | 26.13% | 19.26% | 30.99% |
| $CF_3CCl_2CH_2CF_2H$ | 22.76% | 2.66% | 4.82% |
| $CF_3CCl_2CH=CClH$ | 27.01% | 6.84% | 13.85% |
| $CF_3CCl_2CH_2CCl_2H$ (starting material) | 24.10% | 1.38% | 0.92% |

TABLE 2

Product Characterization from Fluorination of $CF_3CCl_2CH_2CHCl_2$

| Structure | GC-MS | $^1$H NMR (500 MHz, CDCl$_3$) | $^{19}$F NMR (476 MHz, CDCl$_3$) |
|---|---|---|---|
| $CF_3CF_2CH_2CF_2H$ | MS (CI): 183 (M$^+$) | 6.16 (tt, J = 54.6 Hz, 4.5 Hz, 1H)<br>2.75-2.60 (m, 2H) | −86.12 (s, 3F)<br>−116.63 (tt, J = 17.1 Hz, 5.7 Hz, 2F)<br>−114.20 (dm, J = 54.5 Hz, 2F) |
| $CF_3CClFCH_2CF_2H$ | MS (CI): 165 (M$^+$ − Cl) | Obstructed by larger peaks/ too dilute | −83.12 (d, 5.8 Hz, 2F)<br>−113.68 (dm, J = 55.1 Hz, 2F) |
| $CF_3CF_2CH_2CClFH$ | MS (CI): 165 (M$^+$ − Cl) | Obstructed by larger peaks/ too dilute | −82.91 (t, J = 1.9 Hz, 3F)<br>−113.79 (dm, J = 54.5 Hz, 1F) |
| $CF_3CClFCH_2CClFH$ | MS (CI): 214 | 6.49 (ddd, J = 50.3 Hz, 7.8 Hz, 3.1 Hz, 1H) | −83.27 (d, J = 5.9 Hz, 3F)<br>−117.12 (dt, J = 23.3 Hz, 11.3 Hz, 1F)<br>−117.38 (ddd, J = 22.2 Hz, 10.4 Hz, 5.9 Hz, 1F) |
| $CF_3CF_2CH_2CCl_2H$ | MS (CI): 216 (M$^+$) | 6.02 (t, J = 6.1 Hz, 1 H)<br>3.04 (td, J = 16.4 Hz, 6.2 Hz, 2H) | −85.98 (s, 3F)<br>−118.11 (t, J = 16.5 Hz, 2F) |
| $CF_3CCl_2CH_2CF_2H$ | MS (CI): 181 (M$^+$ − Cl) | 6.22 (tt, J = 54.8 Hz, 4.2 Hz, 1H)<br>2.88 (td, J = 13.6 Hz, 4.1 Hz, 2H) | −80.38 (s, 3F)<br>−112.33 (dtq, J = 54.7 Hz, 13.6 Hz, 1.7 Hz, 2F) |
| $CF_3CCl_2CH=CClH$ | MS (CI): 212 (M$^+$) | 6.79 (d, J = 9.3 Hz, 1H)<br>6.50 (d, J = 9.3 Hz, 1H) | −69.89 (s, 3F) |

Example 5

HFO-1336ze and HCFO-1335ze Via Liquid Phase Dehydrohalogenation

NaOH aqueous solution (6 mL, 0.06 mol) is added to $CF_3CF_2CH_2CHClF$ (10 g, 0.05 mol) and water (6.8 mL) at room temperature in the presence of Aliquat® 336 (0.27 g). The reaction temperature is raised to 80° C. after the addition, and gas chromatography is used to monitor the reaction. After two hours, 8 g product (selectivity to E-1336ze 90% and selectivity to Z-1336ze 10%. yield: 98%) was collected in a dry ice trap.

Example 6

HFO-1336ze and HCFO-1335ze Via Liquid Phase Dehydrohalogenation

KOH aqueous solution (6 mL, 0.06 mol) is added to $CF_3CF_2CH_2CHF_2$ (9.2 g, 0.05 mol) and water (6.8 mL) at room temperature in the presence of Aliquat® 336 (0.27 g). The reaction temperature is raised to 80° C. after the addition, and gas chromatography is used to monitor the reaction. After two hours, 7.5 g product (selectivity to E-1336ze 90% and selectivity to Z-1336ze 10%. yield: 92%) was collected in a dry ice trap.

Example 7

HFO-1336ze and HCFO-1335ze Via Liquid Phase Dehydrohalogenation

NaOH aqueous solution (6 mL, 0.06 mol) is added to $CF_3CF_2CH_2CHCl_2$ (10.8 g, 0.05 mol) and water (6.8 mL) at room temperature in the presence of Aliquat® 336 (0.27 g). The reaction temperature is raised to 80° C. after the addition, and gas chromatography is used to monitor the reaction. After 1 hour, 8.5 g product (selectivity to E-1335zd 90% and selectivity to Z-1335zd 10%. yield: 94%) is collected in a dry ice trap.

Example 8

Vinyl chloride (7.4 g, 0.118 mol) was added to the mixture of CFC-113a (100 g, 0.53 mol), Fe powder (0.62 g, 0.011 mol), and triphenyl phosphine (1.41 g, 0.0054 mol) in a 210 mL Hastelloy® reactor. The reactor was heated up to 175° C. for five hours. The mixture was transferred to a container and analyzed by GC to determine the resulting conversion and selectivity. Conversion and selectivity results are listed in Table 3.

Example 9

Vinyl chloride (7.4 g, 0.118 mol) was added to the mixture of CFC-113a (100 g, 0.53 mol), Fe powder (0.62 g, 0.011 mol), and triphenyl phosphine (1.41 g, 0.0054 mol) in a 210 mL Hastelloy® reactor. The reactor was heated up to 150° C. for five hours. The mixture was transferred to a container and analyzed by GC to determine the resulting conversion and selectivity. Conversion and selectivity results are listed in Table 3.

Example 10

Vinyl chloride (14.8 g, 0.236 mol) was added to the mixture of CFC-113a (100 g, 0.53 mol), Fe powder (0.62 g, 0.011 mol), and triphenyl phosphine (1.41 g, 0.0054 mol) in a 210 mL Hastelloy® reactor. The reactor was heated up to 150° C. for five hours. The mixture was transferred to a container and analyzed by GC to determine the resulting conversion and selectivity. Conversion and selectivity results are listed in Table 3.

Example 11

Vinyl chloride (22.6 g, 0.354 mol) was added to the mixture of CFC-113a (100 g, 0.53 mol), Fe powder (0.62 g, 0.011 mol), and triphenyl phosphine (1.41 g, 0.0054 mol) in a 210 mL Hastelloy® reactor. The reactor was heated up to 150° C. for five hours. The mixture was transferred to a container and analyzed by GC to determine the resulting conversion and selectivity. Conversion and selectivity results are listed in Table 3.

Example 12

Iron metal (0.62 g, 0.011 mol) and triphenyl phosphine (1.41 g, 0.0054 mol) can be added into a pressure reactor. Then, $CCl_4$ (100 g, 0.53 mol) can be added to the mixture. The reactor can be evacuated and charged with ethylene (22.6 g, 0.354 mol). Then, the mixture can be heated up to about 150° C. for five hours. After five hours, the resulting mixture can be analyzed by gas chromatography-mass spectrometry (GC-MS).

Example 13

Iron metal (0.62 g, 0.011 mol) and triphenyl phosphine (1.41 g, 0.0054 mol) can be added into a pressure reactor. Then, CFC-113a (100 g, 0.53 mol) can be added to the mixture. The reactor can be evacuated and charged with 3,3,3-trifluoropropene (34 g, 0.354 mol). Then, the mixture can be heated up to about 150° C. for five hours. After five hours, the resulting mixture can be analyzed by GC-MS.

Example 14

Iron metal (0.62 g, 0.011 mol) and triphenyl phosphine (1.41 g, 0.0054 mol) can be added into a pressure reactor. Then, CFC-113a (100 g, 0.53 mol) can be added to the mixture. The reactor can be evacuated and charged with vinyl fluoride (16 g, 0.354 mol). Then, the mixture can be heated to about 150° C. for five hours. After five hours, the resulting mixture can be analyzed by GC-MS.

Example 15

Iron metal (0.62 g, 0.011 mol) and triphenyl phosphine (1.41 g, 0.0054 mol) can be added into a pressure reactor. Then, CFC-113a (100 g, 0.53 mol) can be added to the mixture. The reactor can be evacuated and charged with vinylidene fluoride (22.6 g, 0.354 mol). Then, the mixture can be heated to about 150° C. for five hours. After five hours, the resulting mixture can be analyzed by GC-MS.

Example 16

Iron metal (0.62 g, 0.011 mol) and triphenyl phosphine (1.41 g, 0.0054 mol) can be added into a pressure reactor. Then, CFC-113a (100 g, 0.53 mol) can be added to the mixture. The reactor can be evacuated and charged with allyl chloride (26.9 g, 0.354 mol). Then, the mixture can be heated to about 150° C. for five hours. After five hours, the resulting mixture can be analyzed by GC-MS.

Example 17

Iron metal (0.62 g, 0.011 mol), $FeCl_3$ (0.81 g, 0.005 mol), and triphenyl phosphine (1.41 g, 0.0054 mol) can be added into a pressure reactor. Then, CFC-113a (100 g, 0.53 mol) can be added to the mixture. The reactor can be evacuated and charged with 3,3,3-trifluoropropene (34 g, 0.354 mol). Then the mixture can be heated to about 150° C. for five hours. After five hours, the resulting mixture can be analyzed by GC-MS.

Example 18

Iron metal (0.62 g, 0.011 mol) and triphenyl phosphine (1.41 g, 0.0054 mol) can be added into a pressure reactor. Then, CFC-113a (100 g, 0.53 mol) can be added to the mixture. The reactor can be evacuated and charged with vinylidene chloride (34.3 g, 0.354 mol). Then the mixture can be heated to about 150° C. for five hours. After five hours, the resulting mixture can be analyzed by GC-MS.

Comparative Example 1

Vinyl chloride (7.4 g, 0.118 mol) was added to a mixture of CFC-113a (100 g, 0.53 mol), Fe powder (0.62 g, 0.011 mol), and tributyl phosphate (1.43 g, 0.0054 mol) in a 210 mL Hastelloy® reactor. The reactor was heated up to 175° C. for five hours. The mixture was transferred to a container and analyzed by GC to determine the resulting conversion and selectivity. Conversion and selectivity results are listed in Table 3.

Comparative Example 2

Vinyl chloride (7.4 g, 0.118 mol) was added to a mixture of CFC-113a (100 g, 0.53 mol), $FeCl_3$ (1.39 g, 0.011 mol), and tributyl phosphate (1.43 g, 0.0054 mol) in a 210 mL Hastelloy® reactor. The reactor was heated up to 175° C. for five hours. The mixture was transferred to a container and analyzed by GC to determine the resulting conversion and selectivity. Conversion and selectivity results are listed in Table 3.

Comparative Example 3

Vinyl chloride (6.1 g, 0.098 mol) was added to a mixture of CFC-113a (100 g, 0.53 mol), $CuCl_2.2H_2O$ (2.2 g, 0.013 mol), Cu powder (0.73 g, 0.0115 mol), and $CH_3CN$ (5.2 g, 0.127 mol) in a 210 mL Hastelloy® reactor. The reactor was heated up to 175° C. for five hours. The mixture was transferred to a container and analyzed by GC to determine the resulting conversion and selectivity. Conversion and selectivity results are listed in Table 3.

The following Table 3 provides a summary of exemplary results of Examples 8-11 and Comparative Examples listed above. This table is not meant to be limiting and serves as one example of various aspects of the disclosure. As shown in the exemplary table, in some aspects, an iron and triphenyl phosphine catalytic system for olefin insertion of haloalkanes and/or hydrohaloalkanes provides a high rate of conversion and selectivity according to one or more aspects.

In some aspects, CFC-113a may be used to produce HFC-343mafn via olefin insertion using the iron and triphenyl phosphine catalytic system outlined above. For example, in one aspect, CFC-113a and vinyl chloride are reacted in the presence of iron and triphenyl phosphine at 150° C. for five hours, resulting in 100% conversion and 95% selectivity under such reaction conditions.

TABLE 3

| Examples | CFC-113a:VC | Catalyst | T (° C.) | time (hr) | Conversion/ Selectivity (%) |
|---|---|---|---|---|---|
| 8 | 4.5:1 | Fe/Triphenyl phosphine | 175 | 5 | 100/93 |
| 9 | 4.5:1 | Fe/Triphenyl phosphine | 150 | 5 | 98/93 |
| 10 | 4.5:2 | Fe/Triphenyl phosphine | 150 | 5 | 100/95 |
| 11 | 4.5:3 | Fe/Triphenyl phosphine | 150 | 5 | 100/90 |
| Comparative Example 1 | 4.5:1 | Fe/Tributyl phosphate | 175 | 5 | 80/88 |
| Comparative Example 2 | 4.5:1 | $FeCl_3$/Tributyl phosphate | 175 | 5 | 100/80 |
| Comparative Example 3 | 5.4:1 | $CuCl_2/Cu/CH_3CN$ | 175 | 17 | 61/70 |

According to further aspects, a ratio of 113a:VC is 2.25:1, a ratio of Fe:VC is 0.0465:1, and the ratio of triphenyl phosphine:VC is 0.023:1. In this example of iron catalyzed olefin insertion, the reaction uses less than 5 mol % metal catalyst in the absence of an organic solvent, running at a relatively lower temperature for a relatively shorter time period than the comparative examples 1-3. As such, a percentage of conversion and a percentage of selectivity of the iron and triphenyl phosphine conditions of Examples 8-11 is comparatively greater than the percentages of conversion and selectivity of Comparative Examples 1-3 using a different metal and ligand combination.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges include each and every value within that range.

What is claimed is:

1. A process comprising contacting $CF_3CCl_3$ with $CH_2\!=\!CHX$ in the presence of a catalyst system that consists of metallic iron and a triphenyl phosphine to make $CF_3CCl_2CH_2CHClX$, wherein X=F or Cl, and fluorinating $CF_3CCl_2CH_2CHClX$ by reaction with HF in the presence of a fluorination catalyst wherein fluorination is conducted in the gas phase to make $CF_3CF_2CH\!=\!CHF$ and $CF_3CF_2CH\!=\!CHCl$, the molar ratio of HF to organic fed to the reaction zone is from 6:1 to 25:1, and the fluorination catalyst is a chrome catalyst.

2. The process of claim 1, wherein $CH_2\!=\!CHX$ is vinyl fluoride.

3. The process of claim 1, wherein $CH_2\!=\!CHX$ is vinyl chloride.

4. The process of claim 1, wherein the catalyst is selected from the group consisting of chromium oxide and chromium oxyfluoride.

5. A process comprising contacting $CF_3CCl_3$ with $CH_2\!=\!CHX$ in the presence of a catalyst system that consists of metallic iron and a triphenyl phosphine to make $CF_3CCl_2CH_2CHClX$, wherein X=F or Cl, and fluorinating $CF_3CCl_2CH_2CHClX$ by reaction with HF in the presence of a fluorination catalyst, wherein the fluorination is conducted in the liquid phase in the presence of a second fluorination catalyst to make a mixture of compounds comprising at least one of $CF_3CF_2CH_2CHF_2$, $CF_3CF_2CH_2CHFC_1$, and $CF_3CF_2CH_2CHCl_2$, and further comprising contacting at least one of $CF_3CF_2CH_2CHF_2$, $CF_3CF_2CH_2CHFC_1$, or $CF_3CF_2CH_2CHCl_2$ with aqueous base in the presence of a phase transfer catalyst to make at least one of $CF_3CF_2CH\!=\!CHF$ or $CF_3CF_2CH\!=\!CHCl$.

6. The process of claim 5, wherein the second fluorination catalyst is selected from the group consisting of $SbF_5$, $SnCl_4$, $TaCl_5$, $TiCl_4$, $NbCl_5$, and fluorinated species thereof.

7. The process of claim 5, wherein the second fluorination catalyst comprises $SbF_5$.

8. The process of claim 5, wherein the aqueous base comprises sodium hydroxide or potassium hydroxide.

\* \* \* \* \*